(12) United States Patent
Knodel et al.

(10) Patent No.: US 8,771,312 B1
(45) Date of Patent: Jul. 8, 2014

(54) ANASTOMOSIS FASTENERS

(75) Inventors: Bryan D. Knodel, Flagstaff, AZ (US);
Luke W. Clauson, Redwood City, CA (US)

(73) Assignee: Cardica, Inc., Redwood City, CA (US)

( * ) Notice: Subject to any disclaimer, the term of this patent is extended or adjusted under 35 U.S.C. 154(b) by 1327 days.

(21) Appl. No.: 11/934,949

(22) Filed: Nov. 5, 2007

(51) Int. Cl.
*A61B 17/08* (2006.01)
*A61D 1/00* (2006.01)

(52) U.S. Cl.
USPC ........................................................ 606/219

(58) Field of Classification Search
CPC ............. A61B 17/064; A61B 17/0642; A61B 17/0643; A61B 17/0644; A61B 17/122
USPC ............. 606/8, 151–158, 213–222, 139, 142, 606/143; 227/175.1–182.1; 411/458, 459, 411/470
See application file for complete search history.

(56) References Cited

U.S. PATENT DOCUMENTS

| | | | |
|---|---|---|---|
| 431,175 | A | 7/1890 | Southwick |
| 718,649 | A | 1/1903 | Morehouse |
| 1,755,538 | A | 4/1930 | Draughton, Jr. |
| 2,111,404 | A | 3/1938 | Pankonin |
| 2,174,708 | A | 10/1939 | Sears et al. |
| 2,323,362 | A | 7/1943 | Weiss |
| 2,345,053 | A | 3/1944 | Judd et al. |
| 2,343,525 | A | 5/1944 | Blodgett |
| 3,049,042 | A | 8/1962 | De Lynn |
| 4,229,888 | A | 10/1980 | Rawson |
| 4,340,331 | A | 7/1982 | Savino |
| 4,485,816 | A | 12/1984 | Krumme |
| 4,592,346 | A | 6/1986 | Jurgutis |
| 4,610,251 | A | 9/1986 | Kumar |
| 4,913,144 | A | 4/1990 | Del Medico |
| 4,960,420 | A | 10/1990 | Goble et al. |
| 5,062,753 | A | 11/1991 | Begue |
| 5,297,714 | A | 3/1994 | Kramer |
| 5,314,427 | A | 5/1994 | Goble et al. |
| 5,324,307 | A | 6/1994 | Jarrett et al. |
| 5,465,895 | A | 11/1995 | Knodel et al. |
| 5,489,058 | A | 2/1996 | Plyley et al. |
| 5,507,776 | A | 4/1996 | Hempel |
| 5,535,935 | A | 7/1996 | Vidal et al. |
| 5,562,241 | A | 10/1996 | Knodel et al. |
| 5,586,711 | A | 12/1996 | Plyley et al. |
| 5,662,258 | A | 9/1997 | Knodel et al. |
| 5,667,527 | A | 9/1997 | Cook |
| 5,690,629 | A | 11/1997 | Asher et al. |
| 5,816,471 | A | 10/1998 | Plyley et al. |
| 5,833,698 | A | 11/1998 | Hinchliffe et al. |
| 5,878,938 | A | 3/1999 | Bittner et al. |
| 5,899,904 | A | 5/1999 | Errico et al. |

(Continued)

*Primary Examiner* — Melanie Tyson
(74) *Attorney, Agent, or Firm* — Cardica, Inc.

(57) ABSTRACT

A fastener suitable for anastomosis procedures may include a base, at least two sharp tines extending from the base, and at least one blunt wing extending from the base. The base may have a perimeter, and the tines and the wings may be arranged in alternating sequence along that perimeter. A method for performing anastomosis between a graft vessel and a target vessel, may include stapling the end of the graft vessel to the side of the target vessel, and deploying at least one fastener into tissue at least at one end of the anastomosis, wherein the fastener includes a plurality of tines and at least one wing, wherein each wing compresses the wall of the graft vessel against the outer surface of the target vessel without penetrating either of the graft vessel and the target vessel.

16 Claims, 3 Drawing Sheets

(56) References Cited

U.S. PATENT DOCUMENTS

| | | |
|---|---|---|
| 5,976,159 A | 11/1999 | Bolduc |
| 5,984,949 A | 11/1999 | Levin |
| 5,993,464 A | 11/1999 | Knodel |
| 6,036,700 A | 3/2000 | Stefanchik et al. |
| 6,165,204 A | 12/2000 | Levinson et al. |
| 6,187,009 B1 | 2/2001 | Herzog et al. |
| 6,187,019 B1 | 2/2001 | Stefanchik |
| 6,193,734 B1 | 2/2001 | Bolduc et al. |
| 6,209,773 B1 | 4/2001 | Bolduc et al. |
| 6,514,263 B1 | 2/2003 | Stefanchik et al. |
| 6,520,973 B1 | 2/2003 | McGarry |
| 6,530,932 B1 | 3/2003 | Swayze |
| 6,726,695 B2 | 4/2004 | Tong |
| 6,811,555 B1 * | 11/2004 | Willis et al. .............. 606/153 |
| 6,890,338 B1 * | 5/2005 | Davis et al. .............. 606/153 |
| 7,267,682 B1 * | 9/2007 | Bender et al. ............ 606/219 |
| 2004/0028502 A1 * | 2/2004 | Cummins .................. 411/457 |

* cited by examiner

ANASTOMOSIS FASTENERS

FIELD OF THE INVENTION

The invention relates to fasteners used to create a connection between blood vessels or other tissue structures.

BACKGROUND

Anastomosis is the operative union of two hollow tissue structures. Vascular anastomosis between blood vessels creates or restores blood flow between them. When a patient suffers from coronary artery disease (CAD), an occlusion or stenosis in a coronary artery restricts blood flow to the heart muscle. In order to treat CAD, anastomosis is performed between a graft vessel and the affected coronary artery in order to bypass the occlusion and restore adequate blood flow to the heart muscle. This surgical procedure is known as a coronary artery bypass graft (CABG). Anastomosis may be performed in other surgical contexts, such as carotid artery bypass surgery or microvascular surgery. An anastomosis tool may be used to connect the two tissue structures, which may be referred to as the graft vessel and the target vessel. As one example of an anastomosis tool, U.S. patent application Ser. No. 11/054,265, filed on Feb. 9, 2005 (the "'265 application"), which is hereby incorporated by reference in its entirety, described an anastomosis tool including a staple holder and an anvil. In the context of CABG, the target vessel may be a coronary artery.

BRIEF DESCRIPTION OF THE DRAWINGS

The use of the same reference symbols in different figures indicates similar or identical items.

DETAILED DESCRIPTION

Figure 1:
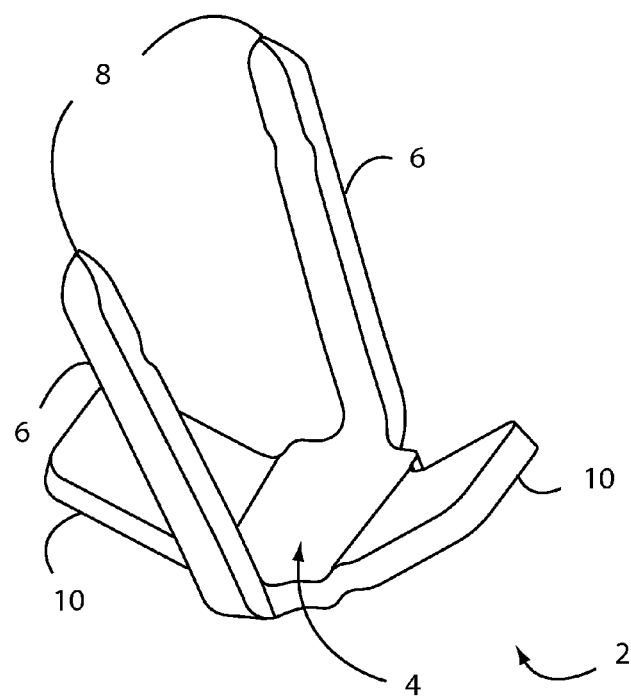
FIG. 1 is a perspective view of an exemplary anastomosis fastener.
Figure 2:
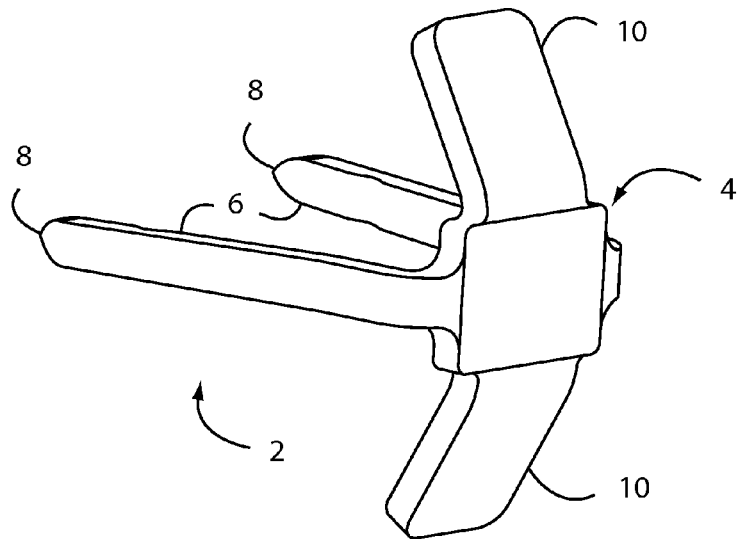
FIG. 2 is another perspective view of the fastener of FIG. 1.

Referring to FIGS. 1-2, an exemplary anastomosis fastener 2 is shown. The fastener 2 is a staple, but the fastener could be a clip or other type of fastener. The fastener 2 includes a generally rectangular base 4, where most or all of the base 4 is substantially planar and substantially the same thickness. Alternately, the base 4 is shaped differently. For example, the base 4 may be substantially square or trapezoidal, or may have different thicknesses at different locations along its surface. As another example, the base 4 may be substantially linear rather than substantially planar. Alternately, the base 4 of the fastener 2 may be curved such that it has substantially no planar surfaces. For example, the base 4 of the fastener 2 may take the form of a right cylindrical tube cut in half lengthwise. Alternately, the base 4 may have any other suitable shape.

The fastener 2 may be fabricated from 316L stainless steel. Thus, the tines 6 are plastically deformable. Alternately, the fastener 2 may be formed from a different type of stainless steel. Alternately, the fastener 2 may be formed from a different biocompatible material or combination of biocompatible materials. For example, the fastener 2 may be formed from a nickel-titanium alloy, or from a non-metallic material. The fastener 2 may be plastically deformable or elastically deformable, depending on the material utilized. Advantageously, the fastener 2 may be substantially 0.05 inches long, 0.04 inches wide, and 0.02 inches in height. These dimensions are small enough to allow the fastener 2 to be used for anastomosis of a graft vessel to a coronary or a carotid artery, for end-to-end microvascular anastomosis, and in other applications involving small or delicate tissue structures. Alternately, the fastener 2 may be sized differently.

Two tines 6 may extend from opposite edges of the base 4 of the fastener 2. Each tine 6 may extend from a location substantially at the midpoint of the corresponding edge of the base 4, as shown in FIGS. 1-2. Optionally, more than two tines 6 may extend from the base 4, from any edge of the base 4 or from any other location on the base 4. Where additional tines 6 are used, the base 4 of the fastener 2 may be longer and/or shaped differently than it would be if two tines 6 were used. One or more of the tines 6 may be substantially the same thickness as the base 4, particularly where the base 4 and tines 6 are formed from a single sheet or piece of material. All of the tines 6 may be shaped substantially the same. Alternately, the tines 6 may be shaped differently from one another. The cross-section of each tine 6 may be rectangular, circular or any other suitable shape. All of the tines 6 may have substantially the same cross-section. Alternately, the tines 6 may have different cross sections. One or more of the tines 6 may be tapered toward its free end 8. One or more of the tines 6 may be tapered to a greater degree in proximity to its free end 8 in order to provide a sharp tooth or point at the free end 8. Alternately, or in addition, the free end 8 of at least one tine 6 is sharpened. Alternately, at least one tine 6 may be small enough in cross-section that its free end 8 is small enough to penetrate tissue readily, without being sharpened or tapered. Further, if tapered, each tine 6 need not be tapered symmetrically or in a linear or constant manner. All of the tines 6 may be tapered in substantially the same manner. Alternately, the tines 6 may be tapered differently from one another.

Two wings 10 may extend from opposite edges of the base 4 of the fastener 2. One end of each wing 10 is connected to the base 4, and the other end of each wing 10 is a free end spaced apart from the base 4. The wings 10 advantageously extend from different edges of the base 4 than the tines 6. The tines 6 and the wings 10 may be arranged in alternating sequence along the perimeter of the base 4. Alternately, the tines 6 and wings 10 may be arranged differently relative to the base 4. Each wing 10 may be substantially as wide as the edge of the base 4 from which it extends. Alternately, at least one wing 10 may have a different width. Optionally, a single wing 10, or more than two wings 10, may extend from the base 4, from any edge of the base 4 or from any other location on the base 4. Where additional wings 10 are used, the base 4 of the fastener 2 may be longer and/or shaped differently than it would be if two wings 10 were used. One or more of the wings 10 may be substantially the same thickness as the base 4, particularly where the base 4 and wings 10 are formed from a single sheet or piece of material. Each wing 10 may be generally rectangular in shape. Alternately, the wings 10 may be shaped differently. The wings 10 may all be shaped in the same manner, or may be shaped differently from one another. The wings 10 may be blunt. The surfaces of the wings 10 may be smooth, or may be rough or otherwise surfaced to promote engagement with tissue.

The fastener 2 of FIGS. 1-2 may be held and deployed from any suitable stapler. As one example, the fastener 2 may be held and deployed from the staple holder of the '265 application. The tines 6 of each fastener 2 may be deformed against an anvil, such as described in the '265 application. A fastener 2 may be urged into contact with the anvil, causing the tines 6 to deform plastically toward one another, or away from one another. The direction of deformation of one or more tines 6 may be determined at least in part by the interaction between one or more tines 6 and the anvil.

Figure 3:
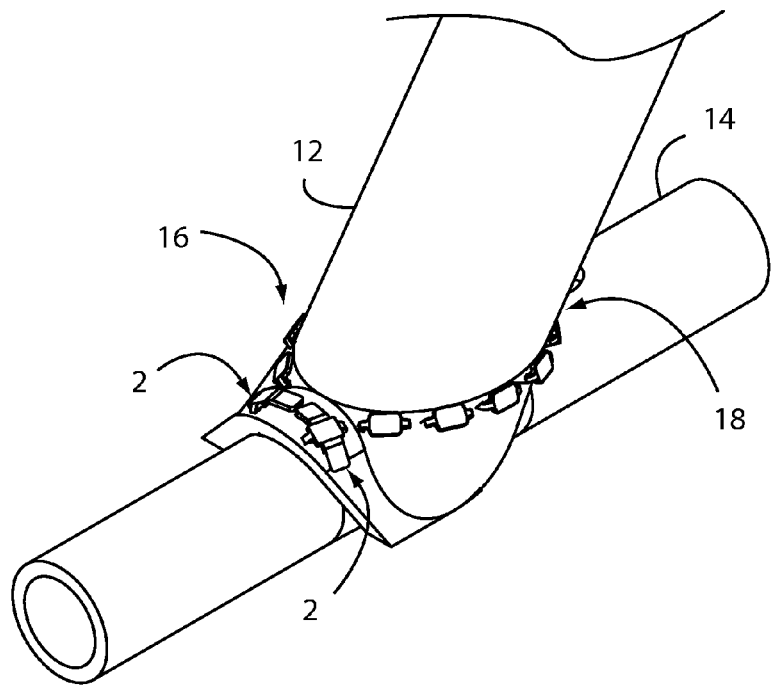
FIG. 3 is a perspective view of an anastomosis between the end of a graft vessel and the side of a target vessel, utilizing the fastener of FIGS. 1-2 at the toe of the anastomosis.
Figure 4:
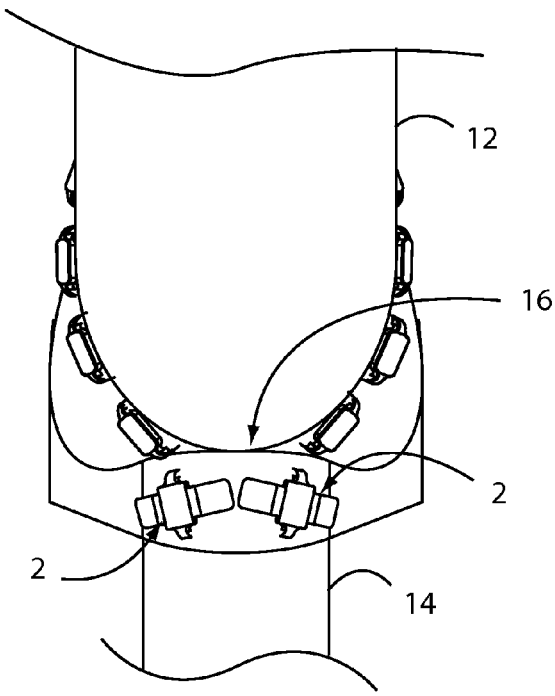
FIG. 4 is a top view of the anastomosis of FIG. 3.

Referring also to FIGS. 3-4, the fasteners 2 may be used advantageously at the toe 16 of an end-to-side anastomosis between the end of a graft vessel 12 and the side of a target vessel 14. Where the graft vessel 12 forms an angle other than perpendicular to the target vessel 14, the toe 16 of the anastomosis is the end of the anastomosis at which the outer surface of the graft vessel 12 forms an obtuse angle with the outer surface of the target vessel 16. The heel 18 of the anastomosis is the opposite end of the anastomosis, at which the outer surface of the graft vessel 12 forms an acute angle with the outer surface of the target vessel 14. The end of the graft vessel 12 may be stapled to the side of the target vessel 14, or otherwise connected to the side of the target vessel 14. Conventional surgical staples may be used to staple the vessels 12, 14 together, rather than the fasteners 2. Two fasteners 2 may be placed at the toe 16 of an anastomosis. If so, the fasteners 2 may be oriented such that a wing 10 of each fastener 2 is oriented toward a wing 10 of the other. As a result, the wings 10 compress the wall of the graft vessel 12 against the outer surface of the target vessel 14, promoting sealing of the vessels 12, 14 against one another. The wings 10 are blunt, and do not penetrate through the vessels 12, 14. In contrast, the tines 6 penetrate through the wall of the graft vessel 12, as well as the wall of the target vessel 14. The fasteners 2 may be oriented generally laterally across the target vessel 14, as seen most clearly in FIG. 4. As a result, a wing 10 of one fastener 2 comes close to the wing 10 of the other fastener 2 at the tip of the toe 16. Consequently, those wings 10 compress the wall of the graft vessel 12 against the wall of the target vessel 14 at the tip of the toe 16, promoting sealing of the toe 16 of the anastomosis. Two fasteners 2 may be placed at the heel 18 of the anastomosis, in generally the same manner, to promote sealing of the heel 18. Alternately, one fastener 2, or three or more fasteners 2, are placed at the toe 16 and/or heel 18 of the anastomosis. The fasteners 2 may be used along any other portion of the anastomosis, if desired. Alternately, the fasteners 2 may be used in a different type of anastomosis. Alternately, the fasteners 2 may be used for surgical procedures other than anastomosis.

Figure 5:
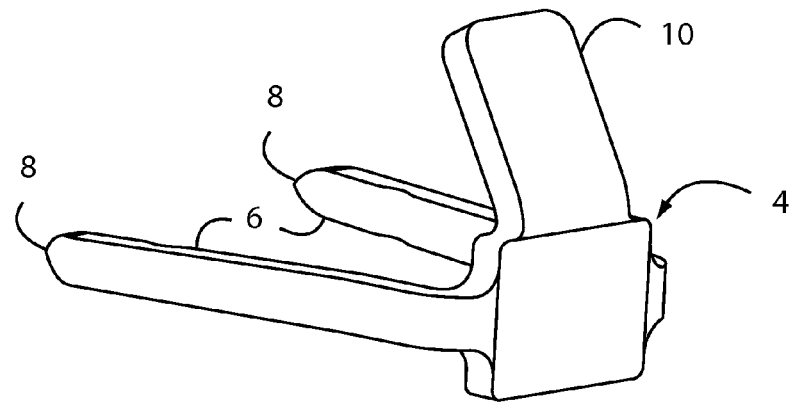
FIG. 5 is a perspective view of another example of an anastomosis fastener.

Referring to FIG. 5, another exemplary fastener 2 is shown. This fastener 2 has a single wing 10, but in other respects is the same as or similar to the fastener 2 of FIGS. 1-2. Two fasteners 2 such as shown in FIG. 5 may be placed at the toe 16 of the anastomosis as shown in FIGS. 3-4, where the wing 10 of each fastener 2 is oriented toward the other. In this way, the wings 10 compress tissue of the graft vessel 12 against the outer surface of the target vessel 14 at the tip of the toe 16 of the anastomosis. Alternately, the fastener 2 may be used at the heel 18 of the anastomosis, or in any other part of the anastomosis or other suitable surgical application. The wing 10 of the fastener 2 of FIG. 5 may be the same length as the wings 10 of the fastener 2 of FIGS. 1-2. Alternately, the wing 10 of the fastener 2 of FIG. 5 may be a different length than the wings 10 of the fastener 2 of FIGS. 1-2.

Figure 6:
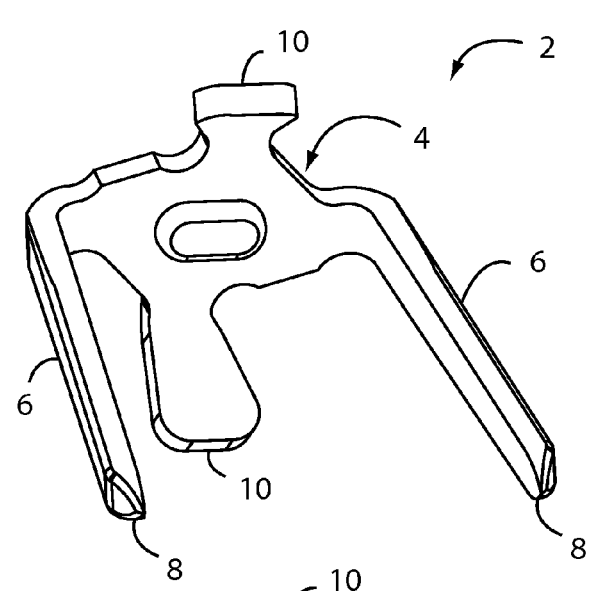
FIG. 6 is a perspective view of another example of an anastomosis fastener.
Figure 7:
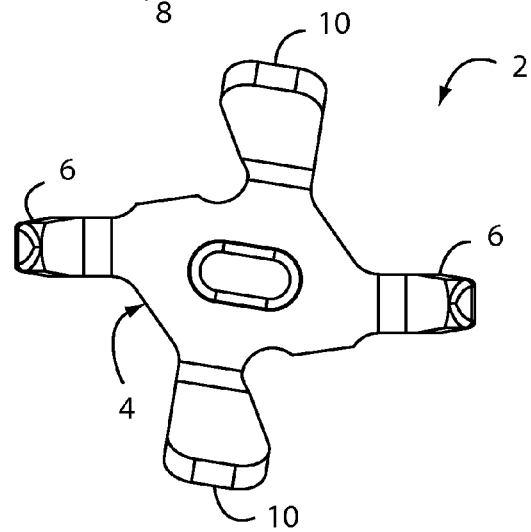
FIG. 7 is an end view of the fastener of FIG. 6.

Referring to FIGS. 6-7, another exemplary fastener 2 is shown. The fastener 2 includes two wings 10, each of which may be generally trapezoidally shaped. The free end of at least one wing 10 may be wider than the end attached to the base 4. Alternately, the free end of at least one wing 10 may be narrower than the end attached to the base 4. The wings 10 are offset from one another relative to the base 4. That is, each wing 10 extends from the base 4 such that the longitudinal centerline of each wing 10 is positioned on a different side of a line that bisects the base 4 and extends through both edges of the base 4 from which the wings 10 extend. As a result, the fastener 2 is not bilaterally symmetrical. Two fasteners 2 such as shown in FIGS. 6-7 may be placed at the toe 16 of the anastomosis as shown in FIGS. 3-4, where a wing 10 of each fastener 2 is oriented toward the other. In this way, the wings 10 compress tissue of the graft vessel 12 against the outer surface of the target vessel 14 at the tip of the toe 16 of the anastomosis. Alternately, the fastener 2 may be used at the heel 18 of the anastomosis, or in any other part of the anastomosis or other suitable surgical application.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A fastener, comprising:
    a base having a substantially continuous outer edge and a substantially continuous solid surface within substantially all of the area defined by said outer edge;
    at least two tines extending from said outer edge, wherein said tines are sharp; and
    at least one wing extending from said outer edge, wherein said at least one wing is blunt, and wherein the at least one wing is non-coplanar with the base, and
    wherein an angle at which the at least one wing extends from said outer edge is different than an angle at which the tines extend from said outer edge.

2. The fastener of claim 1, wherein two wings extend from said base, and wherein said wings are offset from one another.

3. The fastener of claim 1, wherein said at least one wing is generally rectangular.

4. The fastener of claim 1, wherein said at least one wing is generally trapezoidal.

5. The fastener of claim 4, wherein at least one said trapezoidal wing has an end attached to said base and a free end, wherein said free end is wider than the end attached to said base.

6. The fastener of claim 1, wherein said base is generally rectangular.

7. The fastener of claim 6, wherein two wings extend from opposite sides of said base.

8. The fastener of claim 6, wherein two tines extend from opposite sides of said base.

9. The fastener of claim 1, wherein each said wing has substantially the same length.

10. The fastener of claim 1, wherein two wings extend from the base, and wherein said wings extend from different sides of the base than the tines.

11. The fastener of claim 1, wherein the angle at which the at least one wing extends from said outer edge is less than the angle at which the tines extend from said outer edge.

12. A fastener for performing anastomosis between a graft vessel and a target vessel, comprising:
- a base having an outer perimeter;
- two tines extending from said base, wherein said tines are sharp; and
- two wings extending from said base, wherein said wings are blunt, and wherein the wings are non-coplanar with each other;
- wherein said tines and said wings are arranged in alternating sequence along said outer outer perimeter of said base such that each said tine is adjacent to two said wings along said perimeter and each said wing is adjacent to two said tines along said outer perimeter, and
- wherein an angle at which said wings extend from said base is less than an angle at which said tines extend from said base.

13. The fastener of claim 12, wherein said tines are configured to penetrate both the graft vessel and the target vessel, and said wings are configured to penetrate neither the graft vessel nor the target vessel.

14. The fastener of claim 12, wherein said two wings are offset from one another.

15. The fastener of claim 12, wherein said two wings are generally rectangular.

16. The fastener of claim 12, wherein said base is generally rectangular.

* * * * *